(12) United States Patent
Akahoshi et al.

(10) Patent No.: US 8,685,645 B2
(45) Date of Patent: Apr. 1, 2014

(54) SCREENING METHOD AND VECTOR, VECTOR LIBRARY, AND ASSAY KIT USED THEREFOR

(75) Inventors: Eiichi Akahoshi, Tokyo (JP); Mitsuko Ishihara, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 12/886,642

(22) Filed: Sep. 21, 2010

(65) Prior Publication Data

US 2011/0244471 A1 Oct. 6, 2011

(30) Foreign Application Priority Data

Mar. 31, 2010 (JP) ................................. 2010-082873

(51) Int. Cl.
*C12Q 1/68* (2006.01)
*C12N 15/00* (2006.01)
*C12N 15/64* (2006.01)

(52) U.S. Cl.
USPC .................. 435/6.1; 435/320.1; 435/91.4

(58) Field of Classification Search
None
See application file for complete search history.

(56) References Cited

U.S. PATENT DOCUMENTS 6,410,314 B1 6/2002 Baiker et al.

FOREIGN PATENT DOCUMENTS

| JP | 10-502535 | 3/1998 |
| JP | 2000-23672 | 1/2000 |
| JP | 2000-201680 | 7/2000 |
| JP | 2004-537280 | 12/2004 |

OTHER PUBLICATIONS

Butel et al., Cell and Molecular Biology of Simian Virus 40: Implications for Human Infections and Disease, Journal of the National Cancer Institute, vol. 91, No. 2, Jan. 20, 1999.*
Boshard et al., A Very Strong Enhancer Is Located Upstream of an Immediate Early Gene of Human Cytomegalovirus, Cell, vol. 41, 521-530, Jun. 1985.*
QC specifications, by Invitrogen, Mammalian Expression Vectors, retrieved on Feb. 8, 2012 from the following website: http://tools.invitrogen.com/content/sfs/productnotes/F_071215_MammalianExpressionVectors.pdf.*
The book enetiled "Drosophila: A practical approach" authored by D.B. Roberts—2nd ed., Publisher Oxford: IRL Press, Publication year 1998—Chapter 5, p. 131, "Enhancer Traps" by CJ O'Kane.*
Thomas Chittenden, et al., "Regulated Replication of an Episomal Simian Virus 40 Origin Plasmid in COS7 Cells", Journal of Virology, Nov. 1991, p. 5944-5951.
Office Action issued Mar. 12, 2013 in Japanese Patent Application No. 2010-082873 (with English translation).

* cited by examiner

*Primary Examiner* — Jim Ketter
*Assistant Examiner* — Reza Ghafoorian
(74) *Attorney, Agent, or Firm* — Oblon, Spivak, McClelland, Maier & Neustadt, L.L.P.

(57) ABSTRACT

According to one embodiment, a method of screening an enhancer and/or a promoter, includes culturing a host cell into which an amplifiable vector is introduced, extracting the vector from the host cell and obtaining the DNA fragment from the extracted vector, wherein the vector includes a DNA fragment to be determined, a gene that is functionally linked downstream of the DNA fragment and encodes a protein to initiate self-replication, and a gene that encodes a replication origin sequence.

9 Claims, 5 Drawing Sheets

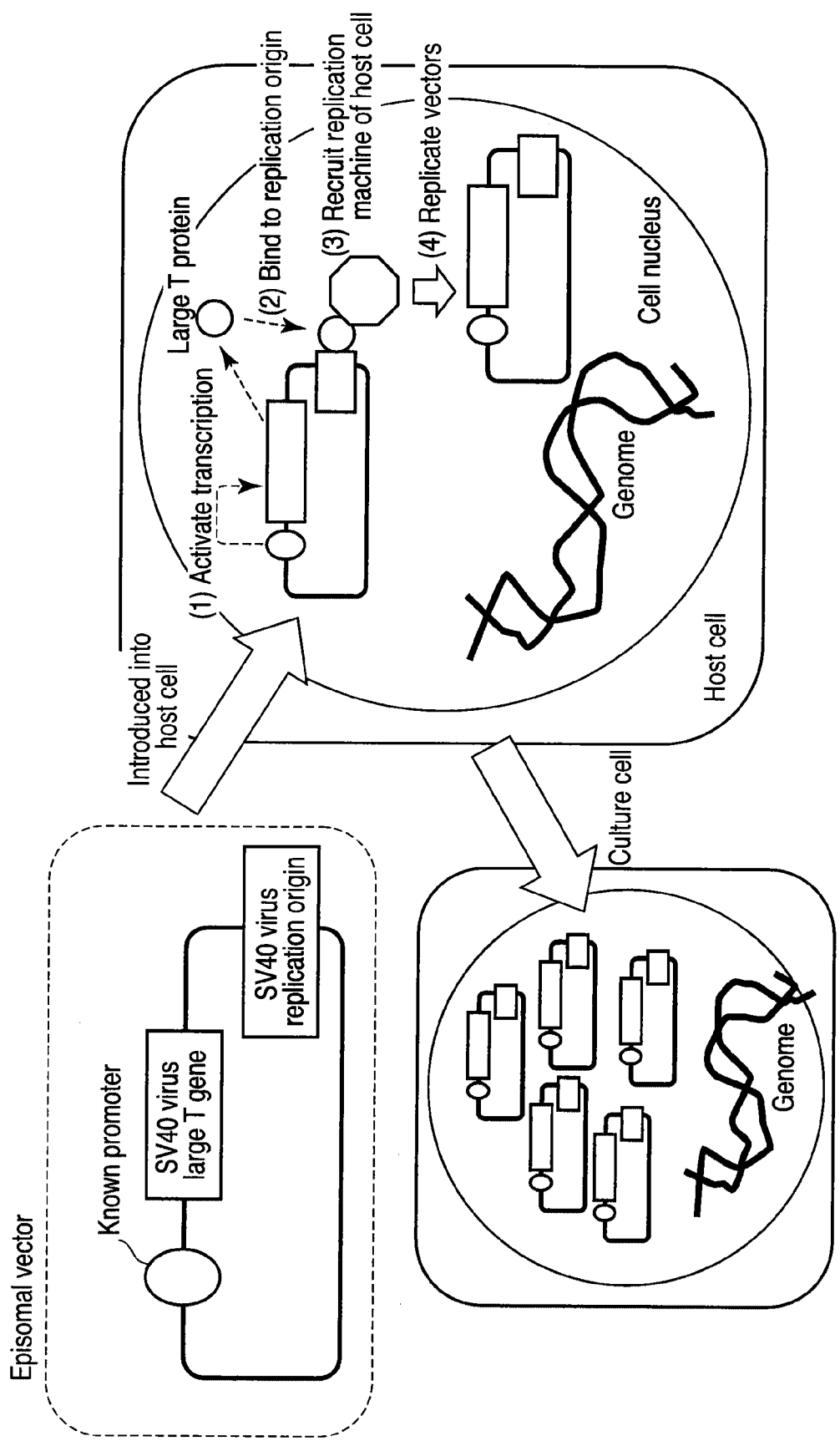
F I G. 1

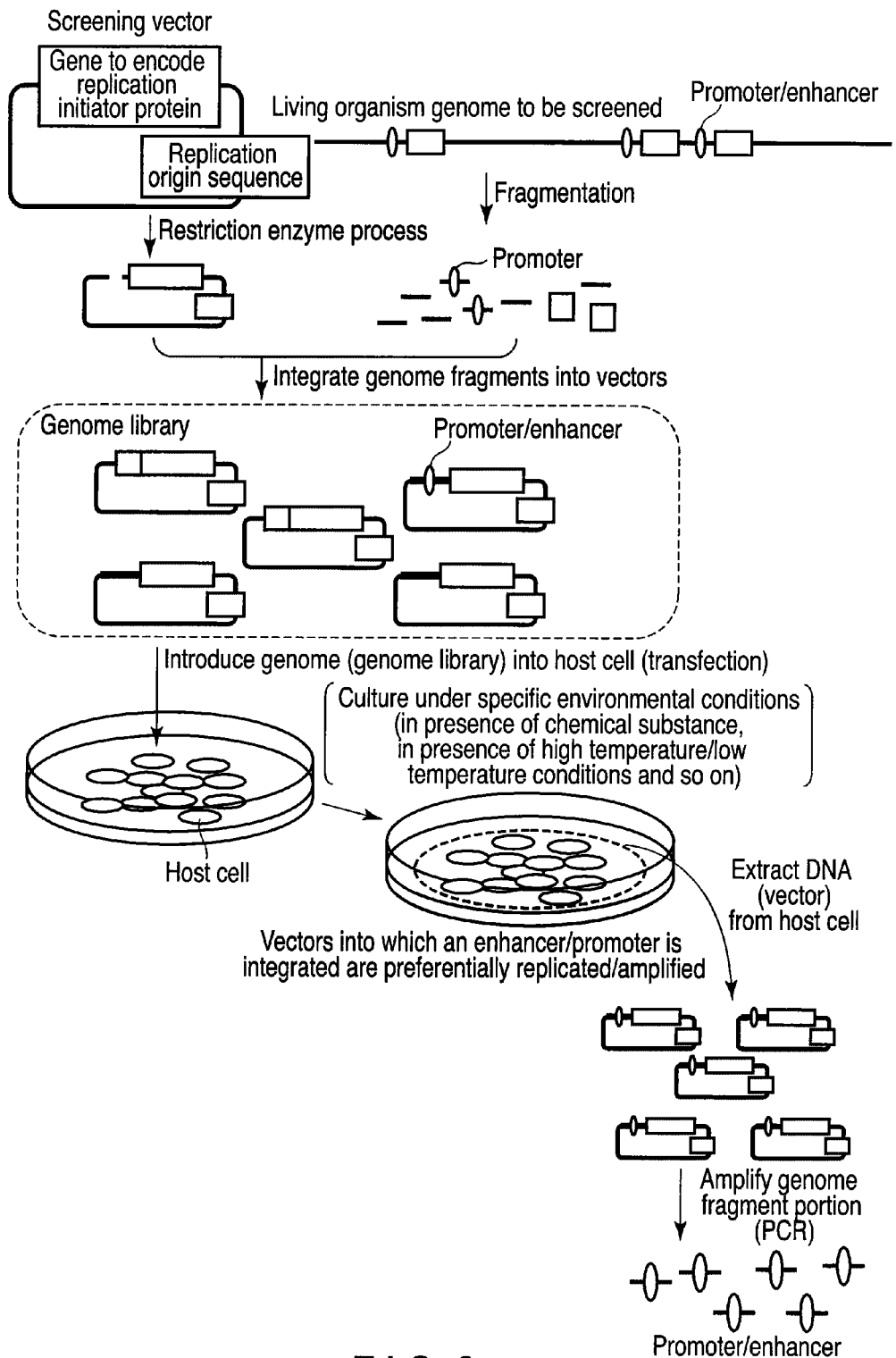
F I G. 2

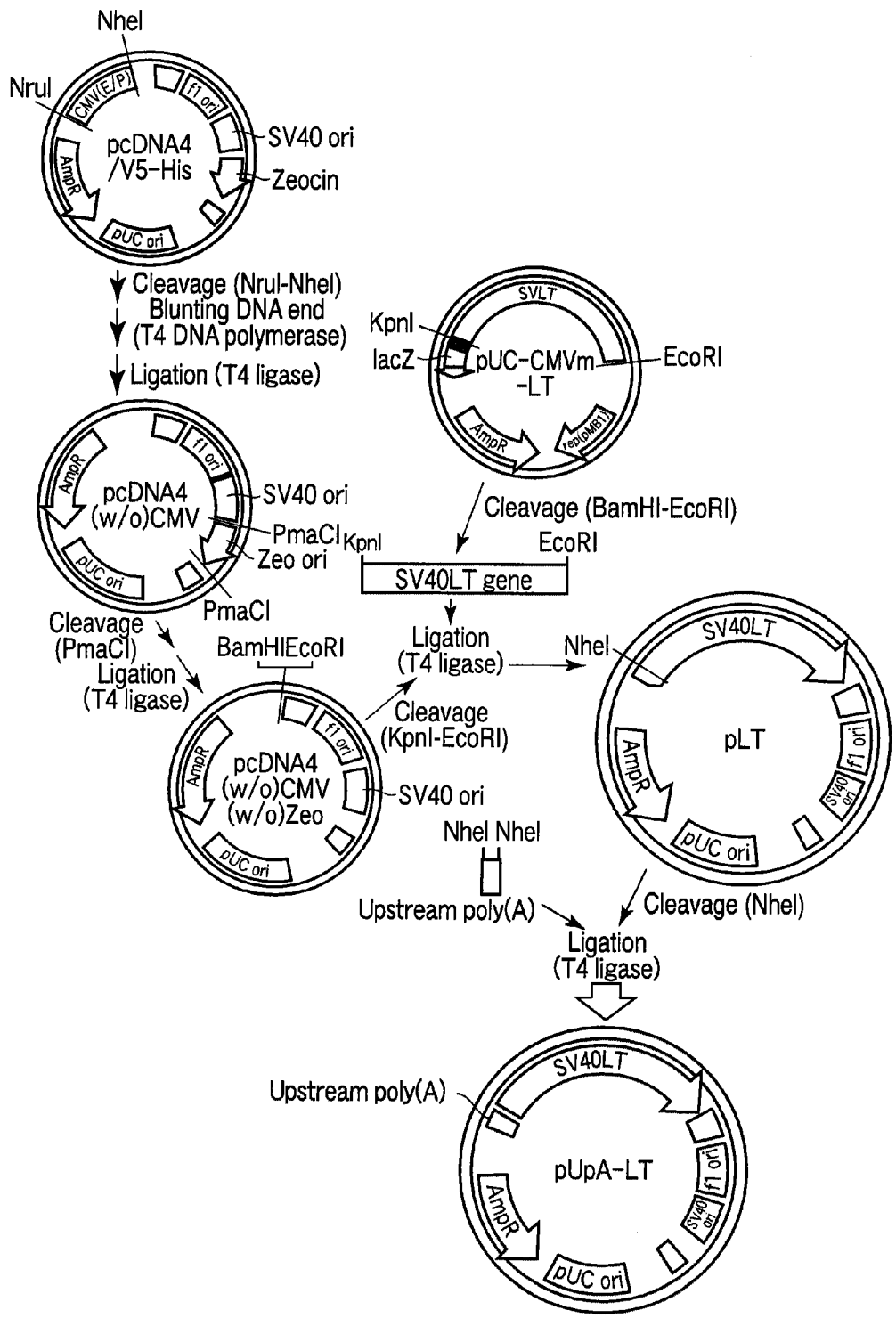
F I G. 3

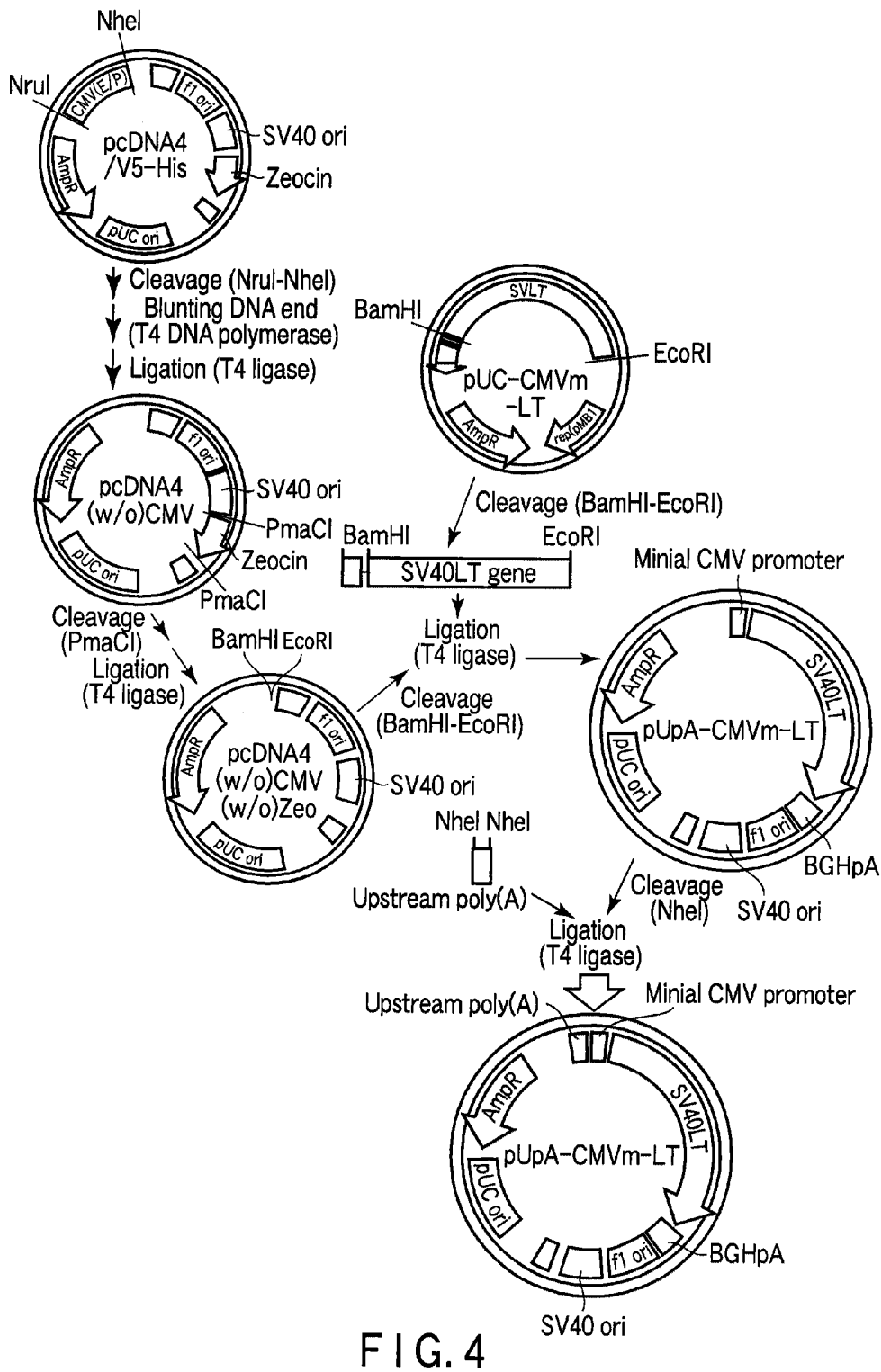
F I G. 4

SCREENING METHOD AND VECTOR, VECTOR LIBRARY, AND ASSAY KIT USED THEREFOR

CROSS-REFERENCE TO RELATED APPLICATIONS

This application is based upon and claims the benefit of priority from Japanese Patent Application No. 2010-082873, filed Mar. 31, 2010; the entire contents of which are incorporated herein by reference.

FIELD

Embodiments described herein relate generally to a method of screening enhancers and/or promoters.

BACKGROUND

Living organisms activate transcriptions of suitable genes to various stimuli received from their environments thereof. Accordingly, suitable proteins are synthesized to adapt to various environments. The above transcriptions of genes are controlled by nucleotide sequences in the vicinity of the genes arrangement on genomes of living organisms. Such nucleotide sequences are called enhancers or promoters. Enhancers and/or promoters become an index to know the state of living organisms in response to stimuli from their environment. Thus, enhancers and/or promoters can effectively be used in a wide range of fields such as the diagnosis of disease, development of therapeutic agents, and detection of hazardous substances. Therefore, the development of technology to screen useful environment specific enhancers and/or promoters from genomes of living organisms has been demanded.

Such methods of screening include the shotgun screening method and the enhancer trap method. The shotgun screening method is a method that is simple in its operation, but its probability of acquiring a promoter is low. According to this method, a vector having a fragmented genome integrated upstream of a marker gene is introduced into a host cell to screen an enhancer and/or a promoter by marker activity provided to the cell by the vector. The enhancer trap method is a time-consuming method of screening due to complex operations because it is necessary to clone cells. According to this method, marker genes that do not have any enhancer and/or promoter are introduced into a cell to be randomly integrated onto a genome. Because only marker genes integrated into the vicinity of an enhancer and/or a promoter are transcribed, enhancers and/or promoters are screened with a high probability from cells cloned using marker activity as an index.

The shotgun screening method and the enhancer trap method can effectively be used for organism species whose genome size is relatively small. However, in the case of screening intended for organism species whose genome size is relatively large, for example, for human beings (genome size: about 3 billion base pairs) or mice (about 3.3 billion base pairs), these methods have problems in terms of simplicity and effectiveness.

BRIEF DESCRIPTION OF THE DRAWINGS

FIG. 1 is a scheme diagram showing workings of an episomal vector inside a cell;
FIG. 2 is a scheme exemplifying a method of screening;
FIG. 3 is a scheme exemplifying a preparation method of a vector;
FIG. 4 is a scheme exemplifying the preparation method of a vector.

DETAILED DESCRIPTION

Figure 5:
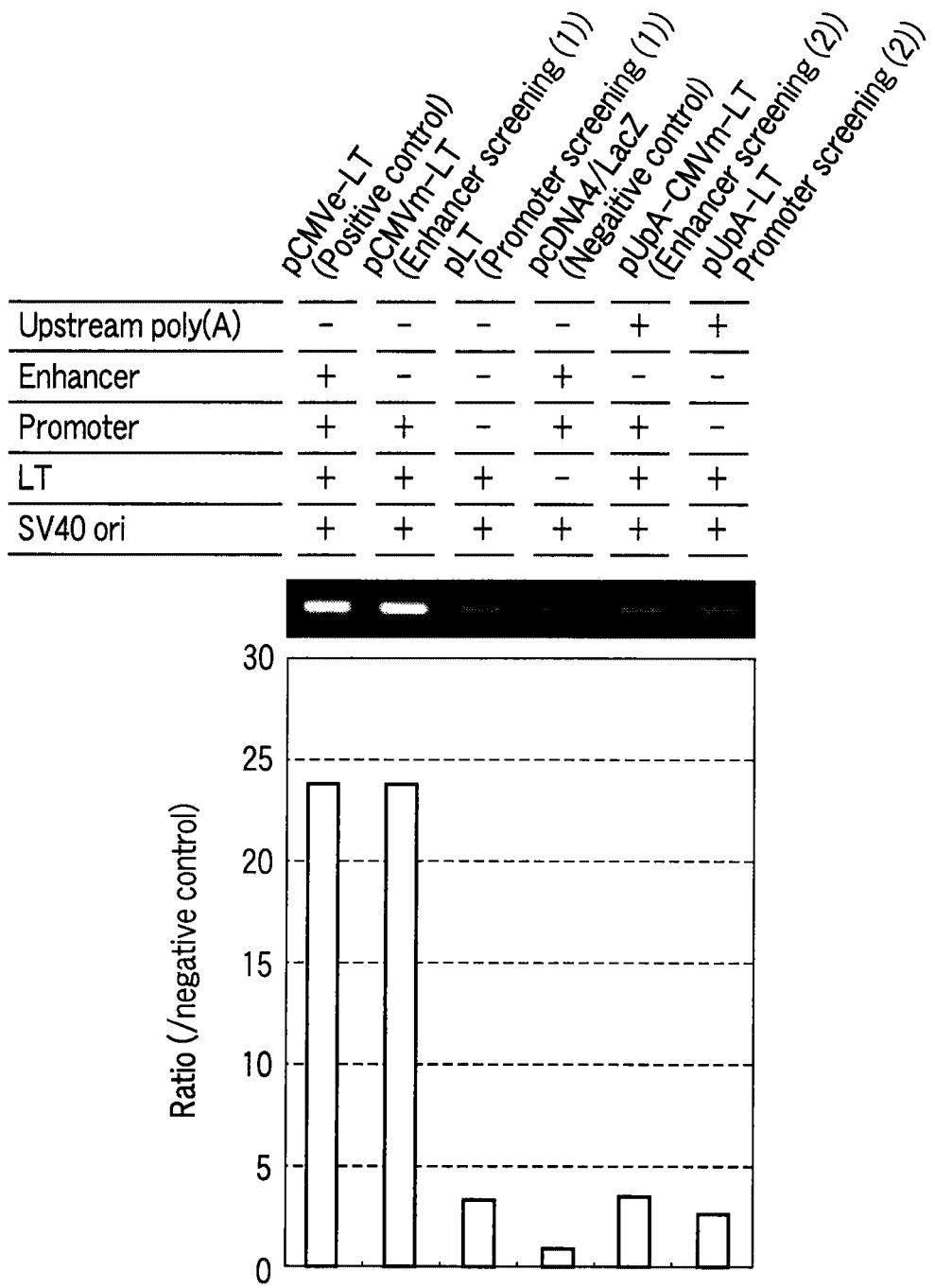
FIG. 5 is a graph exemplifying a vector amount inside the cell.

In general, according to one embodiment, a method of screening an enhancer and/or a promoter, the method comprising:
(A) culturing a host cell into which an amplifiable vector is introduced,
  the amplifiable vector comprising;
  (a) a DNA fragment to be determined,
  (b) a gene that is functionally linked downstream of the DNA fragment and encodes a protein to initiate self-replication if the DNA fragment is the promoter or the enhancer, and
  (c) a gene that encodes a replication origin sequence recognized by the protein in the (b),
(B) extracting the vector from the host cell; and
(C) obtaining the DNA fragment from the extracted vector.

According to another embodiment, in the above method of screening is characterized in that only vector is selectively amplified, the vector having a DNA fragment that have enhancer and/or promoter activity, owing to an acting of the protein transcribed and translated from the gene in the (b) in the culture in the (B).

According to another embodiment, a vector used by the above method of screening can be provide, the vector comprising:
(a) a DNA fragment to be determined;
(b) a gene that is functionally linked downstream of the DNA fragment and encodes a protein to initiate self-replication if the DNA fragment is a promoter or an enhancer; and
(c) a gene that encodes a replication origin sequence recognized by the protein in the (b).

According to another embodiment, a vector library used by the above method of screening can be provide, the vector library consisting essentially of a plurality of vectors, and one vector for constituting the vector library, comprising:
(a) a DNA fragment to be determined;
(b) a gene that is functionally linked downstream of the DNA fragment and encodes a protein to initiate self-replication if the DNA fragment is a promoter or an enhancer; and
(c) a gene that encodes a replication origin sequence recognized by the protein in the (b);
Wherein
  an overall length sequence of a genome of one target living organism or a partial sequence of a genome containing at least one promoter or enhancer sequence is distributed and contained in the sequence of the DNA fragments in the (a), the DNA fragments included in the plurality of vectors respectively.

According to another embodiment, an assay kit used by the above method of screening can be provide, the assay kit comprising:
a vector comprising;
(a) a DNA fragment to be determined;
(b) a gene that is functionally linked downstream of the DNA fragment and encodes a protein to initiate self-replication if the DNA fragments the promoter or the enhancer; and
(c) a gene that encodes a replication origin sequence recognized by the protein in the (b);

a reagent that extracts the vector from a host cell; and an amplification primer set to amplify a nucleotide sequence of the DNA fragment.

According to another embodiment, a means for screening enhancers and/or promoters more easily and efficiently can be provided.

The vector that can be used is, for example, a plasmid vector.

A method of screening enhancers and/or promoters can use, for example, a plasmid vector.

"Functionally linked" and "operably linked" mean that linkage is such that each gene to be bound can execute a function intended as purpose. "Functionally linked" and "operably linked" may be used interchangeably.

A "promoter" may be a nucleotide sequence having a binding sequence of RNA polymerase. The promoter may be any nucleotide sequence having a function to adjust and/or activate the transcription of a gene functionally linked thereto.

An "enhancer" is a nucleotide sequence linked to a promoter and having a function to enhance activation of the transcription of a gene by the promoter.

Cells that can be used as "host cells" may be cells derived from a primate including a human being and monkey or cells derived from a rodent including a mouse and rat. These cells may be established cell lines or primary cultured cells. Examples of established cell lines derived from primates include, for example, the Huh-7 cell derived from human hepatic cancer, Huh-7T1, Huh-7T2, Huh-7T3, Huh-7T5, Huh-7T7, Huh-7T8, Huh-7T9, and Huh-7T10, which are sub-clones of the Huh-7 cell, the HepG2 cell derived from human hepatic cancer, the Jurkat cell derived from human T-cell leukemia, the MCF-7 cell derived from human breast cancer, and the CV-1 cell derived from green monkey kidney. Examples of established cell lines derived from rodents include, for example, the Hepa-1 cell derived from mouse hepatic cancer, the Neuro-2a cell derived from mouse neuroblastoma, and the PC12 cell derived from rat phenochromocytoma. Examples of primary cultured cells derived from a primate or rodent include, for example, primary cultured cells, tissue stem cells, and embryonic stem cells derived from organs such as the liver and the brain.

A "DNA fragment to be determined" may be a nucleic acid fragment containing a candidate sequence of a promoter and/or an enhancer or a nucleic acid fragment consisting essentially of such a candidate sequence. For example, a "DNA fragment to be decided" may be an artificial sequence designed randomly and/or a sequence derived from an animal and/or a plant present in nature and/or a natural occurring sequence, or a sequence consisting essentially of such sequences. In a candidate sequence of enhancers and/or promoters, it does not matter how much promising is each enhancer and/or promoter as a candidate.

"Depending on enhancer and/or promoter activity" means dependence on presence/absence of activity of a DNA fragment to be determined whether or not an enhancer and/or a promoter and/or on the magnitude of activity. If a DNA fragment has such activity, a vector containing the DNA fragment is amplified by self-replication inside a host cell. Therefore, whether a DNA fragment in question is an enhancer and/or a promoter can be determined based on presence/absence of vector amplification and/or the degree of amplification. Activity of a DNA fragment may depend on environmental conditions. For example, a DNA fragment may exhibit activity only in the presence of a substance such as a particular compound or component. Alternatively, a DNA fragment may exhibit activity in accordance with the range of pH values. Presence/absence of activity or a change in magnitude thereof in accordance with the environment of a field in which cells are present is called "environment specific activation".

The method of screening enhancers and/or promoters may use a plasmid vector. The plasmid vector in the present invention will be described below.

The plasmid vector in the present invention contains a gene that encodes a replication initiator protein, which is a protein to initiate DNA replication, and a recognition sequence that recognizes and binds the protein. The plasmid vector can be self-replicated and/or amplified inside a host cell.

The plasmid vector is generally called also as an episomal vector or extrachromosomal plasmid vector. As the replication initiator protein and recognition sequence integrated into an episomal vector, for example, virus-derived agents such as simian virus 40 (SV40) and Epstein-Barr virus (EBV) are known and these agents may be used.

For SV40, the replication initiator protein may be a large T antigen (LT) and the recognition sequence may be an SV40 ori sequence. For Epstein-Barr virus, the replication initiator protein may be an EBNA protein and the recognition sequence may be an EB virus latent replication origin (oriP). The episomal vector into which these replication initiator proteins and recognition sequences are integrated is amplified by self-replication in a cell of a primate such as a human being or monkey as a host cell.

The vector may be a vector having a large T antigen gene of mouse polyoma virus (PyV) as a gene that encodes the replication initiator protein and a PyV core origin sequence as the replication origin sequence. For example, an episomal vector using a cell of rodents such as mice as a host cell may be prepared.

FIG. 1 shows an example of a general episomal vector. FIG. 1 is a diagram showing the self-replication mechanism of a vector into which the replication origin sequence and recognition sequence of SV40 are integrated. The episomal vector used in this case contains the large T antigen (LT) gene of SV40 and the replication origin sequence (SV40 ori) of SV40 functionally linked to promoters or enhancers/promoters by being integrated thereinto.

An overview of findings forming the basis of the method of screening enhancers and/or promoters will be provided in FIG. 1.

If the episomal vector shown in FIG. 1 is introduced into a host cell, the LT gene is transcribed and translated inside the host cell to synthesize an LT protein. The LT protein is bound to SV40 on of the vector to recruit a DNA replication machine of the host cell. Replication of the vector is thereby initiated inside the host cell. Accordingly, the episomal vector is amplified by self-replication inside the host cell. As described here, for self-replication and amplification of the episomal vector inside the host cell, an LT protein needs to be synthesized after the LT gene being transcribed and translated.

By making use of this finding, that is, the finding that the LT gene needs to be transcribed and translated for amplification of the episomal vector inside the host cell, environment specific enhancers, promoters, and enhancers/promoters on a genome of a living organism can efficiently be screened.

The vector used by the above method of screening enhancers and/or promoters is a vector containing (a) a DNA fragment to be determined (b) a gene that is functionally linked downstream of (a) and encodes a protein to initiate self-replication if (a) is a promoter or enhancer, and (c) a gene that encodes a replication origin sequence recognized by the protein in (b).

FIG. 2 shows an example of a used vector and provides an overview of the method of screening enhancers and/or promoters using the vector.

For the screening, a screening vector into which a gene that encodes a replication initiator protein and a recognition sequence of the replication initiator protein are integrated is used. However, in contrast to the above general episomal vector, no promoter is integrated or only promoters having only an extremely weak transcription activity are integrated upstream of the gene to encode a replication initiator protein. Therefore, the LT gene is not sufficiently transcribed even if the episomal vector is introduced into a host cell. Consequently, the vector cannot be self-replicated and amplified inside the host cell.

A DNA fragment (that is, a genome fragment) for the purpose of acquisition of enhancers or promoters is integrated upstream of the replication initiator protein of the screening vector. By randomly integrating a genome fragment of a living organism to be screened, for example, a genome library for screening may be prepared. Such a genome library is also an aspect of the present invention.

If the genome fragment or the genome library is introduced into a host cell and cultured, transcription of the LT gene does not occur from a vector into which a genome fragment having no transcription activation ability of a gene is integrated. Thus, such a vector cannot be amplified inside a host cell. In contrast, in a vector into which a genome fragment having transcription activity of a gene, that is, a genome fragment containing promoters, enhancers, or promoters/enhancers is integrated, transcription of the LT gene occurs. This is translated to synthesize an LT protein. Accordingly, the vector is amplified by self-replication inside the host cell. As a result, only a vector into which a genome fragment containing promoters, enhancers, or promoters/enhancers is integrated is selectively amplified inside a host vector into which a genome library is introduced.

DNA (vector) is extracted from such a cell and, if necessary, a genome fragment site integrated into the vector is amplified by a publicly known amplification method such as PCR. Promoters, enhancers, or promoters/enhancers can thereby be screened from a genome efficiently. Accordingly, when compared with the conventional genomic shotgun method or enhancer trap method, screening can be made simpler and more efficient.

Details of the vector, genome library, and method of screening promoters and/or enhancers using the vector and genome library provided in the present invention will be described below.

A) Enhancer and/or Promoter Screening Vector

The enhancer and/or promoter screening vector has a gene to encode a replication initiator protein and a replication origin sequence recognized by the protein. The replication initiator protein may be any protein that could function to initiate DNA replication in a host cell used for screening. For example, the replication initiator protein may be a protein derived from a virus infecting a host cell for amplification or a protein of the same animal species as the host cell. Alternatively, the replication initiator protein may be a protein derived from different animal species.

The replication origin sequence may be any nucleotide sequence that recognizes a replication initiator protein transcribed and translated from a gene integrated into a vector and also functions to initiate replication. For example, the replication origin sequence may be derived from the same source as the living organism species of the replication initiator protein or a different source.

For example, when a cell of a primate such as a human being or monkey is used as a host cell, a vector containing the large T antigen gene of SV40 as a gene to encode a replication initiator protein and the SV40 ori sequence as a replication origin sequence may be prepared as a screening vector. Alternatively, a vector containing the EBNA protein of EBV as a replication initiator protein and the EB virus latent replication origin (oriP) as a replication origin sequence may be prepared.

When a cell of a rodent such as a mouse or rat is used as a host cell, a vector containing the large T antigen gene of mouse polyoma virus (PyV) as a gene to encode a replication initiator protein and the PyV core origin sequence as a replication origin sequence may be prepared as a screening vector.

An example of preparing a promoter and/or enhancer screening vector into which a large T antigen protein of SV40 and a replication origin sequence recognized by the protein are integrated will be described below as an example when a cell of a primate such as a human being or monkey is used as a host cell.

Sequence No. 1 shows the nucleotide sequence of the LT antigen gene of SV40. The nucleotide sequence of the LT gene does not have to perfectly match the nucleotide sequence of Sequence No. 1 as long as the function to initiate replication of the LT protein is not lost, and may contain, for example, mutations of one to several deletions, additions and/or substitutions.

Sequence No. 2 shows the nucleotide sequence of SV40 ori, which is a replication origin sequence of SV40. This nucleotide sequence does not have to perfectly match the nucleotide sequence of Sequence No. 2 as long as the function initiate replication is not lost, and may contain, for example, mutations of one to several deletions, additions and/or substitutions.

The LT gene and SV40 on may be acquired by a known genetic engineering technique. For example, the LT gene or SV40 on may be acquired after amplification by PCR using a primer set specific to the nucleotide sequence. Alternatively, the entire nucleotide sequence may be synthesized, or the LT gene or SV40 on already integrated in a vector may be used.

Sequence Nos. 5 and 6 both show examples of the primer set used for amplification of the LT gene by PCR. Vectors to integrate these genes may newly be prepared or vectors on the market may be used.

pUC-CMVm-LT shown in FIG. 3 is an example of the vector into which the LT gene is already integrated. The LT gene can be obtained by digesting the vector using a restriction enzyme. By integrating the LT gene obtained in this manner into a vector on the market having the SV40 on sequence, a promoter screening vector may be prepared.

For example, pcDNA4/V5-His (Invitrogen) can be cited as an example of the vector having the SV40 on sequence. A vector on the market may be used unchanged or after an unnecessary nucleotide sequence being removed. An example of the promoter screening vector prepared in this manner is pLT in FIG. 3. In the vector, there is neither promoter nor enhancer upstream of the LT gene. Thus, the vector can be used for screening of a genome fragment containing a promoter having a transcription activation ability of a gene.

To prepare an enhancer screening vector, a promoter having only an extremely weak transcription activity may be integrated upstream of the LT gene of a promoter screening vector. The core promoter (minimal CMV promoter) of cytomegalovirus described in Sequence No. 5 can be cited as an example of such a promoter.

The nucleotide sequence of a promoter may be acquired by a known genetic engineering technique. For example, the nucleotide sequence may be acquired after amplification by PCR using a primer set specific to the nucleotide sequence. Alternatively, the entire nucleotide sequence may be synthesized, or the nucleotide sequence already integrated in a plasmid vector may be used.

pUC-CMVm-LT shown in FIG. 3 is an example of the vector in which the minimal CMV promoter is integrated upstream of the LT gene. The minimal CMV promoter and the LT gene linked thereto can be acquired from the vector by digesting the vector. An enhancer screening vector can be prepared by integrating the minimal CMV promoter::LT gene (Sequence No. 4) obtained in this manner into a vector having the SV40 on sequence. An example of the enhancer screening vector prepared in this manner is pCMVm-LT in FIG. 3.

In the above promoter and/or enhancer vector, no promoter is integrated or only promoters having only an extremely weak transcription activity are integrated upstream of the gene to encode a replication initiator protein. Thus, when the vector is introduced into a host cell, no replication initiator protein is in principle transcribed or even if transcribed, the amount of transcription is very small. Thus, the replication initiator protein is hardly synthesized, which makes self-replication and amplification of the vector less likely. However, depending on the vector used for integration of a gene to encode a replication initiator protein, transcription of the gene may occur when not induced to synthesize a sufficient amount of the replication initiator protein and, as a result, the vector may unintentionally be amplified by self-replication.

To prevent such transcription of a gene when not induced, a transcription termination signal sequence (Upstream poly (A) sequence) may be integrated upstream of the gene. Accordingly, no transcription of a gene that encodes a replication initiator protein by inappropriate transcription will occur. The transcription termination signal sequence may be any nucleotide sequence that functions in a host cell and whose transcription termination ability of a gene is high.

As an example of the transcription termination signal sequence, for example, a poly A addition signal sequence of SV40 shown in Sequence No. 3 may be used. The transcription termination signal sequence may be acquired by a known genetic engineering technique. For example, the transcription termination signal sequence may be acquired after amplification by PCR using a primer set specific to the nucleotide sequence. Alternatively, the entire nucleotide sequence may be synthesized, or the transcription termination signal sequence already integrated in a plasmid vector may be used.

An example in which the SV40 poly (A) signal sequence is integrated into the screening vector described above as the Upstream poly (A) sequence will be shown below. The SV40 poly A addition signal sequence is amplified by PCR using a primer set described in Sequence Nos. 7 and 8 and digested by an appropriate restriction enzyme. For a vector :pLT having no promoter, an upstream portion of the LT gene that encodes a replication initiator protein is digested by an appropriate restriction enzyme. Next, the above SV40 poly A addition signal sequence similarly digested by the restriction enzyme is integrated.

pUpA-LT shown in FIG. 3 is an example of the vector in which Upstream poly (A) is integrated upstream of the LT gene. This vector may be used as a promoter screening vector. When pCMVm-LT is used as a vector, an upstream portion of the minimal CMV promoter of the vector is digested by an appropriate restriction enzyme and, like the case of pLT, the SV40 poly A addition signal sequence is integrated.

pUpA-CMVm-LT shown in FIG. 3 is an example of the vector in which Upstream poly (A) is integrated upstream of the LT gene. This vector may be used as a promoter screening vector.

B) Genome Library

A genome fragment obtained by randomly fragmenting a genome of a living organism to be screened may be integrated into the vector for enhancer and/or promoter screening described in A) as a DNA fragment to be determined. If such an integrated genome library is used, a sequence having the enhancer and/or promoter function present on a genome can be screened.

The genome to be integrated into a vector is preferably a genome of living organism species from which a host cell into which the vector is introduced is derived or a genome of related living organism species.

Cells to constitute a genome library may derive from any living organism species such as eukaryotic cells, prokaryotic cells, animal cells, and plant cells. Examples thereof include, for example, blood corpuscles, liver cells, nerve cells, tissue stem cells, and embryonic stem cells. Alternatively, cells to constitute a genome library may not be limited to specified cells and may be, for example, an organ or tissue constituted by a plurality of cells. The target living organism used for constructing a genome library may be any living organism. For example, the target living organism may be a eukaryote, prokaryote, animal, plant, bacterium, virus, yeast and the like. Examples of the eukaryote include, for example, a primate such as a human being or monkey and a rodent such as a mouse or rat. The target living organism is not limited to living organisms and may be a virus. The method of screening enhancers and/or promoters can favorably screen also eukaryotes whose genome size is large.

If, for example, a host cell is derived from a human being, the genome to be integrated into a vector is preferably a genome of a human being, which is the same species as that of the host cell, or of a monkey, which is a relative species of the human being. However, the present invention is not limited to this and a genome of a rodent such as a mouse or rat may also be integrated.

Alternatively, instead of a genome of a living organism, a randomly synthesized nucleotide sequence may be integrated.

As shown in FIG. 2, a genome fragment may be integrated upstream of a gene to encode a replication initiator protein. In the case of, for example, pLT, which is a promoter screening vector described in A), a genome fragment may be integrated into a site digested by an appropriate restriction enzyme upstream of the LT gene.

In the case of, for example, pUpA-LT obtained by integrating the Upstream poly (A) sequence into pLT, a genome fragment may be integrated into a site digested by an appropriate restriction enzyme downstream of the Upstream poly (A) sequence and upstream of the LT gene. In the case of, for example, pCMVm-LT, which is an enhancer screening vector, a genome fragment may be integrated into a site digested by an appropriate restriction enzyme upstream of the LT gene. In the case of, for example, pUpA-CMVm-LT obtained by integrating the Upstream poly (A) sequence into pCMVm-LT, a genome fragment may be integrated into a site digested by an appropriate restriction enzyme downstream of the Upstream poly (A) sequence and upstream of the LT gene.

The genome to be offered for screening may be acquired from a target living organism by a known genetic engineering technique. Alternatively, a genome solution prepared and sold on the market may be purchased. The genome to be used may be an entire genome or a portion thereof. The genome to be used does not need to be necessarily an entire genome.

There is a library obtained by integrating a portion of a genome into a cosmid or bacteria artificial chromosome (BAC) and a clone into which a portion of the target genome is integrated may be selected from such a library. A cosmid or BAC library may be prepared by the user to select a clone into which a portion of the target genome is integrated. Such a clone may also be selected from a library on the market. Alternatively, if a clone into which a portion of the target genome is integrated is on the market, such a clone may be purchased and used.

In a genome library, at least an overall length of a genome of one target living organism may be distributed and contained in a sequence derived from a genome present by being divided into a plurality of vectors, that is, DNA fragments. That is, a sequence obtained by integrating all sequences derived from a genome into one sequence may contain an overall length sequence of the genome of one living organism. Alternatively, a sequence obtained by integrating such sequences into one sequence may consist essentially of the overall length sequence of the genome of one living organism; or, in a genome library, a sequence derived from the genome present by being divided into a plurality of vectors, that is, DNA fragments may be a partial sequence of a genome containing at least one promoter or enhancer sequence. The sequence obtained by such integration contains the overall length of a genome of one living organism or a portion thereof or a sequence of any portion; further, a portion of the sequence of the genome may be overlapped among DNA fragments.

The genome obtained in this manner may be fragmented into appropriate lengths before being integrated into a promoter and/or enhancer screening vector. The length of a genome fragment is preferably about 100 to 5000 base pairs. However, the length thereof is not limited to this range.

A genome may be fragmented by a known genetic engineering technique. Such techniques include, for example, a method of fragmentation by digestion using a restriction enzyme, a method of fragmentation by supersonic waves and/or a method of fragmentation by pipetting. A vector having genome fragments integrated thereinto may be provided as a genome library for promoter and/or enhancer screening. Such a vector may be called a genome library.

C) Promoter and/or Enhancer Screening

In B) described above, a prepared genome library is used so that a sequence functioning as a promoter or enhancer on a genome may be screened.

Such a method of screening will be described below. The flow of the method of screening is as shown in FIG. 2. First, a genome library prepared in B) is introduced into a host cell and cultured for any period.

The host cell used here may be selected in accordance with the gene of the replication initiator protein integrated into the vector used for the construction of the genome library and the type of the replication origin sequence. If the replication initiator protein is the LT protein of SV40 and the replication origin sequence is SV40 ori, or the EBNA protein of EBV and oriP are used, it is preferable to select a cell derived from a primate such as a human being or monkey. Alternatively, if the replication initiator protein is the LT protein of PyV and the replication origin sequence is the PyV core origin sequence, it is preferable to select a cell derived from a rodent such as a mouse. If a used vector functions as intended in a used host cell and the host cell functions as intended, such a combination is considered to be appropriate.

If the combination of a group of screening vectors (that is, a genome library) and a host cell are appropriate, the type of cell is not particularly limited. The host cell may be, for example, an established cell line or primary cultured cell. Moreover, the tissue from which the cell is derived is not particularly limited. The tissue may be selected in accordance with the type of the enhancer and/or promoter to be screened.

A known cell engineering technique may be used as the method to introduce a screening vector into a host cell. The method includes, for example, a method of using cation lipid and a method of using calcium chloride as biochemical methods. As a physiochemical method, for example, an electric terebration method can be cited.

After introducing the vector into the host cell in this manner, the cell is cultured for any period of time. In this culture period, the vector having a genome fragment containing enhancers and/or promoters introduced thereinto is selectively amplified.

To screen environment specific enhancers and/or promoters, a desired environmental stimulus, for example, a chemical substance, the temperature and/or oxidant stress may be provided in the culture period. Accordingly, enhancers and/or promoters corresponding to the stimulus are screened in accordance with the environmental stimulus provided to the cell. After the culture, the vector is extracted from the cell to acquire genome fragments. Accordingly, enhancers and/or promoters in the genome are obtained. In the acquired substance, vectors into which genome fragments containing enhancers and/or promoters are integrated are highly concentrated. After genome fragments are acquired from extracted vectors, a known genetic engineering technique may be used. As a simple method, for example, a method of amplifying a region into which genome fragments are integrated of the vector by PCR can be cited.

Thus, intended enhancers and/or promoters can easily be obtained from the genome of a target living organism by using the genome library prepared in B) described above.

For example, the above genome library may be a vector library, the vector library consisting essentially of a plurality of vectors, and one vector for constituting the vector library, comprising:

(a) a DNA fragment to be determined;

(b) a gene that is functionally linked downstream of the DNA fragment and encodes a protein to initiate self-replication if the DNA fragment is a promoter or an enhancer; and (c) a gene that encodes a replication origin sequence recognized by the protein in the (b); wherein an overall length sequence of a genome of one target living organism or a partial sequence of a genome containing at least one promoter or enhancer sequence is distributed and contained in the sequence of the DNA fragments in the (a), the DNA fragments included in the plurality of vectors respectively.

By providing a vector library of a particular living organism species, the user can easily obtain an enhancer and/or promoter activated depending on environmental conditions according to purposes. If the vector library is used with the above method of screening enhancers and/or promoters, an intended enhancer and/or promoter can be obtained more easily and efficiently.

D) Assay Kit

A kit used for the above method may be provided. Such a kit may be an assay kit comprising a vector containing a vector comprising;

(a) a DNA fragment to be determined;

(b) a gene that is functionally linked downstream of the DNA fragment and encodes a protein to initiate self-replication if the DNA fragments the promoter or the enhancer; and (c) a gene that encodes a replication origin sequence recognized by the protein in the (b);

a reagent that extracts the vector from a host cell; and an amplification primer set to amplify a nucleotide sequence of the DNA fragment.

The example of the reagent to extract a vector may contain at least a proteolytic enzyme and a cytolytic solution and may further contain a vector purification column, a column cleaning fluid, vector eluate and the like. The proteolytic enzyme may be proteinase K. The cytolytic solution may be a buffer solution containing sodium dodecylsulfate and/or a buffer solution containing guanidine.

An example of the amplification primer set may be a primer capable of amplifying nucleic acid found to have enhancer and/or promoter activity by screening. The amplification primer set may contain a forward primer and a reverse primer. The amplification method includes any publicly known amplification method such as the PCR method or LAMP method. The assay kit may further contain a reagent for amplification reaction. Examples of such a PCR primer set include a combination of the nucleotide sequence described in Sequence No. 11 and the nucleotide sequence described in Sequence No. 12 and a combination of the nucleotide sequence described in Sequence No. 11 and the nucleotide sequence described in Sequence No. 13, but the PCR primer set is not limited to these examples.

The assay kit may further contain a vessel to allow a reaction to occur therein and a vessel to make a culture therein. Furthermore, a culture medium for the culture or a buffer may further be contained.

The vector contained in the assay kit may be a vector library obtained by dividing a genome library derived from a particular genome and causing a plurality of vectors to contain the divided vector library.

Thus, a method of screening such enhancers and/or promoters, a method of screening of efficiently acquiring a nucleotide sequence having an enhancer and/or promoter function made environment specifically active from a genome of an intended living organism, and a means capable of screening enhancers and/or promoters more easily and efficiently by vectors, vector libraries, and assay kits used therein are provided.

EXAMPLES

1) Vector Preparation

Promoter screening vectors pLT and pUpA-LT were prepared (FIG. 3). An enhancer/promoter region of cytomegalovirus (CMV) was removed by digesting pcDNA4/V5-HisB (Invitrogen) using NruI/NheI, blunt-ending with T4 DNA polymerase, and ligated by T4 DNA ligase to prepare pcDNA4 (w/o) CMV. Next, after pcDNA4 (w/o) CMV being digested by PmaCI, the Zeocin resistance gene was removed by self-ligation with T4 DNA ligase. Accordingly, a vector :pcDNA4 (w/o) CMV (w/o) Zeo was prepared. pcDNA4 (w/o) CMV (w/o) Zeo obtained by digesting the vector using KpnI/EcoRI and the LT gene (Sequence No. 1) obtained from pUCmCMV-LT after the vector being digested by KpnI/EcoRI were linked by T4 DNA ligase to prepare pLT. pUC-mCMV-LT is a vector having an expression cassette consisting a minimal CMV promoter (Sequence No. 2) synthesized in pUC19 and the LT gene amplified by PCR using Sequence Nos. 5 and 6 integrated thereinto. pUpA-LT was prepared by ligating pLT after being digested by NheI and the Upstream poly (A) sequence after being similarly digested by NheI using T4 DNA ligase. As the Upstream poly (A) sequence, the SV40 poly (A) additional signal sequence (Sequence No. 3) amplified by PCR using a primer set described in Sequence Nos. 7 and 8.

Further, two enhancer screening vectors, pCMVm-LT and pUpA-CMVm-LT were prepared (FIG. 4). These vectors are vectors having the minimal CMV promoter (Sequence No. 2) upstream of the LT gene in pLT and pUpA-LT respectively. First, pcDNA4 (w/o) CMV (w/o) Zeo after being digested by BamHI/EcoRI and an expression cassette (Sequence No. 4) of the minimal CMV promoter::LT gene obtained from pUC-mCMV-LT by digesting BamHI/EcoRI were linked using T4 DNA ligase to prepare pCMVm-LT. This vector after being digested by NheI and the Upstream poly (A) sequence (SV40 poly (A) additional signal sequence, Sequence No. 3) after being similarly digested by NheI were linked using T4 DNA ligase to prepare pUpA-CMVm-LT (FIG. 4). As the Upstream poly (A) sequence, like pUpA-LT, the SV40 poly (A) addition signal sequence (Sequence No. 3) was used.

As a positive control vector, a vector :pCMVe-LT having an enhancer integrated into the above screening vector as a basis was used. This vector was prepared by integrating the LT gene obtained from pUCmCMV-LT into the site of KpnI/EcoRI of pcDNA4/V5-HisB from which Zeocin gene had been removed by digestion using PmaCI.

In addition, pcDNA4/LacZ (Invitrogen) was used as a negative control vector and pTHEn-Luc as a control vector to normalize a transfection efficiency. The former has an enhancer, a promoter, and the SV40 on sequence integrated thereinto, but has no LT gene. Instead of the LT gene, a β-galactosidase gene is integrated thereinto. The latter has no enhancer, no promoter, no SV40 on sequence, and no LT gene.

2) Transfection

Transfection was carried out by the lipofection method using lipofectamine 2000 (Invitrogen). Human hapatoma strain :Huh-7 cells (Health Science Research Resources Bank) were cultured in a 24-well plate at 37° C. in a 5% $CO_2$ atmosphere using a DMEM culture medium containing 10% heat-inactivated fetal bovine serum (number of seeding cells: $2.0 \times 10^4$ cells/well). 1.0 μL of lipofectamine 2000 was added to 50 μL of Opti-MEM culture medium (Invitrogen) and was incubated for five minutes at room temperature. Then, this was mixed with 50 μL of Opti-MEM culture medium in which 0.6 μg of vector (0.1 μg of pCMVe-LT or pCMVm-LT or pLT or pUpA-CMVm-LT or pUpA-CMVw-LT or pcDNA4/V5-His/LacZ, 0.5 μg of pTHEnLuc) was suspended. A lipofectamine/vector solution was thereby prepared. After being incubated for 20 minutes at room temperature, this solution was added to a Huh-7 cell cultured for overnight.

3) Measurement of the Vector Amount in a Cell 24 hours after the transfection, the culture medium of Huh-7 cell was replaced by a new medium. 48 hours thereafter, the culture medium was replaced with a new one. 76 hours thereafter, a DNeasy kit (Qiagen) was used to extract DNA containing vectors from the cell. The culture medium was removed from the culture plate and the cell was washed with phosphate buffer solution (PBS) and then, 500 μL of PBS was added and detached the cell from the flask bottom using a cell scraper. The cell was collected by centrifugation at 10,000 rpm for 3 minutes. 200 μL of PBS, 20 μL of Proteinase K, and 200 μL of AL solution (attached to the kit) were added to the cell and the solution was mixed well by a vortex mixer to lyse the cell by a process caused thereby at 56° C. for 10 minutes. 200 μL of 99.5% ethanol was added to the solution and the solution was mixed well by the vortex mixer before being applied to a DNeasy column. The column was centrifuged to adsorb DNA in the solution by at 8,000 rpm for 1 minute and the column was washed with 500 µL of AW1 solution (attached to the kit) and 500 µL of AW2 solution (attached to the kit) in this order before DNA being eluted by 500 µL of AE solution (attached to the kit). The vector amount in this solution was measured by the semi-quantitative PCR or real-time PCR. A same primer-set was used to amplify all vectors (pLT, pCMVmin-LT, pCMVen-LT, pUpA-CMVm-LT, pUpA-CMVw-LT, and pcDNA4/LacZ) by PCR (Sequence No. 9, Sequence No. 10) excluding a control vector (pTHEn-Luc) was used for the PCR. 20 µL of PCR solution (composition: 1.0 µL of vector extract, 2.0 µL of reaction buffer, 1.6 µL of deoxynucleotide mixed solution, 1.0 µL of primer mixed solution (10 µM each), 0.4 µL of Taq polymerase, and 14.0 µL of bactericidal water) was prepared. Using the PCR solution, the PCR reaction was performing under the following conditions: at 95° C. for 30 seconds, at 56° C. for 30 seconds, and at 72° C. for 30 seconds. FIG. 5 shows a result of electrophoresis of the reaction solution by 0.8% agarose gel. Six days after the introduction, there was no significant difference between the amount of pCMVe-LT (positive control vector) having the CMV enhancer and promoter integrated thereinto and the amount of pCMVm-LT having the minimal promoter integrated thereinto. On the other hand, the amount of pLT having an enhancer and the minimal promoter integrated thereinto, the amount of pUpA-LT having the poly (A) sequence upstream of pLT, and the amount of pUpA-CMVm-LT having the poly (A) sequence upstream of the minimal promoter were $\frac{1}{10}$ or less of the amount of the positive control vector :pCMVe-LT and no different from the amount of the negative control vector :pcDNA4/LacZ. Since the vector amount introduced into the cell is equal, the above example shows that vectors acquire self-replication and amplification abilities by enhancers and promoters being integrated into enhancer/promoter screening vectors. This shows that pUpA-CMVm-LT can be used as an enhancer screening vector and pLT and pUpA-LT as promoter screening vectors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method of screening for an enhancer and/or a promoter, the method comprising:
- (A) culturing a host cell into which an amplifiable plasmid vector is introduced,
  - wherein the host cell does not comprise a T antigen gene of simian virus 40 in its genome,
  - the amplifiable plasmid vector comprising;
    - (a) a DNA fragment to be determined, and a first transcription termination sequence that is functionally linked upstream of the DNA fragment,
    - (b) a minimal CMV promoter that is functionally linked downstream of the DNA fragment,
    - (c) a large T antigen gene of simian virus 40 that is functionally linked downstream of the minimal CMV promoter, and
    - (d) a second transcription termination sequence functionally linked downstream to the large T antigen gene and a sequence that encodes a replication origin sequence of simian virus 40 that is functionally linked downstream to the second transcription termination sequence,
- (B) extracting the vector from the host cell; and
- (C) obtaining the DNA fragment from the extracted vector.

2. The method according to claim 1, previous to the culturing in (A), further comprising (A') introducing the amplifiable vector into the host cell.

3. The method according to claim 1, further comprising (D) sequencing a sequence of the DNA fragment obtained in the (C).

4. The method according to claim 1, wherein the enhancer and/or the promoter is environment-specifically activated.

5. The method according to claim 1, wherein the first and second transcription termination sequences are poly A sequences.

6. The method according to claim 1, wherein the host cell is a cell derived from a human being or a monkey.

7. The method according to claim 1, wherein the DNA fragment in the (a) comprise a random nucleotide sequence of 100 base lengths to 5000 base lengths.

8. The method according to claim 1, wherein the DNA fragment in the (a) consists essentially of a partial sequence of a genome sequence of continuous 100 base lengths to 5000 base lengths.

9. The method according to claim 1, wherein an appearance of activity of the enhancer and/or promoter depends on presence of a chemical substance.

* * * * *

SEQUENCE LISTING

```
<160> NUMBER OF SEQ ID NOS: 13

<210> SEQ ID NO 1
<211> LENGTH: 2132
<212> TYPE: DNA
<213> ORGANISM: Simian virus 40

<400> SEQUENCE: 1
atggataaag ttttaacaga gaggaatctt tgcagctaat ggaccttcta ggtcttgaaa        60
ggagtgcctg ggggaatatt cctctgatga gaaaggcata tttaaaaaaa tgcaaggagt       120
ttcatcctga taaaggagga gatgaagaaa aaatgaagaa aatgaatact ctgtacaaga       180
aaatggaaga tggagtaaaa tatgctcatc aacctgactt tggaggcttc tgggatgcaa       240
ctgagattcc aacctatgga actgatgaat gggagcagtg gtggaatgcc tttaatgagg       300
aaaacctgtt ttgctcagaa gaaatgccat ctagtgatga tgaggctact gctgactctc       360
aacattctac tcctccaaaa aagaagagaa aggtagaaga ccccaaggac tttccttcag       420
aattgctaag tttttttgagt catgctgtgt ttagtaatag aactcttgct tgctttgcta       480
tttacaccac aaaggaaaaa gctgcactgc tatacaagaa aattatggaa aaatattctg       540
taacctttat aagtaggcat aacagttata atcataacat actgtttttt cttactccac       600
acaggcatag agtgtctgct attaataact atgctcaaaa attgtgtacc tttagctttt       660
taatttgtaa aggggttaat aaggaatatt tgatgtatag tgccttgact agagatccat       720
tttctgttat tgaggaaagt ttgccaggtg ggttaaagga gcatgatttt aatccagaag       780
aagcagagga aactaaacaa gtgtcctgga gcttgtaac agagtatgca atggaaacaa       840
aatgtgatga tgtgttgtta ttgcttggga tgtacttgga atttcagtac agttttgaaa       900
tgtgtttaaa atgtattaaa aaagaacagc ccagccacta taagtaccat gaaaagcatt       960
atgcaaatgc tgctatattt gctgacagca aaaaccaaaa aaccatatgc caacaggctg      1020
ttgatactgt tttagctaaa aagcgggttg atagcctaca attaactaga gaacaaatgt      1080
taacaaacag atttaatgat cttttggata ggatggatat aatgtttggt tctacaggct      1140
```

-continued

```
ctgctgacat agaagaatgg atggctggag ttgcttggct acactgtttg ttgcccaaaa    1200
tggattcagt ggtgtatgac tttttaaaat gcatggtgta caacattcct aaaaaaagat    1260
actggctgtt taaaggacca attgatagtg gtaaaactac attagcagct gctttgcttg    1320
aattatgtgg ggggaaagct ttaaatgtta atttgcccct ggacaggctg aactttgagc    1380
taggagtagc tattgaccag ttttttagtag ttttttgagga tgtaaagggc actggagggg    1440
agtccagaga tttgccttca ggtcagggaa ttaataacct ggacaattta agggattatt    1500
tggatggcag tgttaaggta aacttagaaa agaaacacct aaataaaaga actcaaatat    1560
ttccccctgg aatagtcacc atgaatgagt acagtgtgcc taaaacactg caggccagat    1620
ttgtaaaaca aatagatttt aggcccagag attatttaaa gcattgcctg gaacgcagtg    1680 agttttttgtt agaaaagaga ataattcaaa gtggcattgc tttgcttctt atgttaatt    1740 ggtacagacc tgtggctgag tttgctcaaa gtattcagag cagaattgtg gagtggaaag    1800
agagattgga caaagagttt agtttgtcag tgtatcaaaa aatgaagttt aatgtggcta    1860
tgggaattgg agttttagat tggctaagaa acagtgatga tgatgatgaa gacagccagg    1920
aaaatgctga taaaaatgaa gatggtgggg agaagaacat ggaagactca gggcatgaaa    1980
caggcattga ttcacagtcc caaggctcat ttcaggcccc tcagtcctca cagtctgttc    2040
atgatcataa tcagccatac cacatttgta gaggttttac ttgctttaaa aaacctccca    2100
cacctccccc tgaacctgaa cctgaaacat aa                                  2132
```

<210> SEQ ID NO 2
<211> LENGTH: 113
<212> TYPE: DNA
<213> ORGANISM: Cytomegalovirus

<400> SEQUENCE: 2

```
taggcgtgta cggtgggagg cctatataag cagagctggt ttagtgaacc gtcagatccc    60
tggagacgcc atccacgctg ttttgacctc catagaagac accgggaccg atc          113
```

<210> SEQ ID NO 3
<211> LENGTH: 165
<212> TYPE: DNA
<213> ORGANISM: Simian virus 40

<400> SEQUENCE: 3

```
gctagcaata aaatatcttt attttcatta catctgtgtg ttggttttttt gtgtgaatcg    60 atagtactaa catacgctct ccatcaaaac aaaacgaaac aaaacaaact agcaaaatag    120
gctgtcccca gtgcaagtgc aggtgccaga acatttctcg ctagc                    165
```

<210> SEQ ID NO 4
<211> LENGTH: 2265
<212> TYPE: DNA
<213> ORGANISM: Artificial Sequence
<220> FEATURE:
<223> OTHER INFORMATION: Description of Artificial Sequence: Synthetic
      polynucleotide sequence including CMV minimal
      promoter and SV40 large T antigen gene

<400> SEQUENCE: 4

```
ggatcctagg cgtgtacggt gggaggccta tataagcaga gctggtttag tgaaccgtca    60
gatccctgga gacgccatcc acgctgtttt gacctccata agaagacaccg ggaccgatcg    120 gtaccagatg gataaagttt aacagagag gaatctttgc agctaatgga ccttctaggt    180
cttgaaagga gtgcctgggg gaatattcct ctgatgagaa aggcatattt aaaaaaatgc    240
```

```
aaggagtttc atcctgataa aggaggagat gaagaaaaaa tgaagaaaat gaatactctg      300
tacaagaaaa tggaagatgg agtaaaatat gctcatcaac ctgactttgg aggcttctgg      360
gatgcaactg agattccaac ctatggaact gatgaatggg agcagtggtg gaatgccttt      420
aatgaggaaa acctgttttg ctcagaagaa atgccatcta gtgatgatga ggctactgct      480
gactctcaac attctactcc tccaaaaaag aagagaaagg tagaagaccc caaggacttt      540
ccttcagaat tgctaagttt tttgagtcat gctgtgttta gtaatagaac tcttgcttgc      600
tttgctattt acaccacaaa ggaaaaagct gcactgctat acaagaaaat tatggaaaaa      660
tattctgtaa cctttataag taggcataac agttataatc ataacatact gttttttctt      720
actccacaca ggcatagagt gtctgctatt aataactatg ctcaaaaatt gtgtacccttt      780 agctttttaa tttgtaaagg ggttaataag gaatatttga tgtatagtgc cttgactaga      840
gatccatttt ctgttattga ggaaagtttg ccaggtgggt taaaggagca tgattttaat      900
ccagaagaag cagaggaaac taaacaagtg tcctggaagc ttgtaacaga gtatgcaatg      960
gaaacaaaat gtgatgatgt gttgttattg cttgggatgt acttggaatt tcagtacagt     1020
tttgaaatgt gtttaaaatg tattaaaaaa gaacagccca gccactataa gtaccatgaa     1080
aagcattatg caaatgctgc tatatttgct gacagcaaaa accaaaaaac catatgccaa     1140
caggctgttg atactgtttt agctaaaaag cgggttgata gcctacaatt aactagagaa     1200
caaatgttaa caaacagatt taatgatctt ttggatagga tggatataat gtttggttct     1260
acaggctctg ctgacataga agaatggatg gctggagttg cttggctaca ctgtttgttg     1320
cccaaaatgg attcagtggt gtatgacttt ttaaaatgca tggtgtacaa cattcctaaa     1380
aaaagatact ggctgtttaa aggaccaatt gatagtggta aaactacatt agcagctgct     1440
ttgcttgaat tatgtggggg gaaagcttta aatgttaatt tgcccttgga caggctgaac     1500
tttgagctag gagtagctat tgaccagttt ttagtagttt ttgaggatgt aaagggcact     1560
ggaggggagt ccagagattt gccttcaggt cagggaatta ataacctgga caatttaagg     1620
gattatttgg atggcagtgt taaggtaaac ttagaaaaga acacctaaa taaagaact      1680 caaatatttc ccctggaat agtcaccatg aatgagtaca gtgtgcctaa acactgcag      1740 gccagatttg taaacaaat agattttagg cccagagatt atttaaagca ttgcctggaa      1800
cgcagtgagt ttttgttaga aaagagaata attcaaagtg gcattgcttt gcttcttatg     1860
ttaatttggt acagacctgt ggctgagttt gctcaaagta ttcagagcag aattgtggag     1920
tggaaagaga gattggacaa agagtttagt ttgtcagtgt atcaaaaaat gaagtttaat     1980
gtggctatgg gaattggagt tttagattgg ctaagaaaca gtgatgatga tgatgaagac     2040
agccaggaaa atgctgataa aaatgaagat ggtgggggaga agaacatgga agactcaggg     2100
catgaaacag gcattgattc acagtcccaa ggctcatttc aggcccctca gtcctcacag     2160
tctgttcatg atcataatca gccataccac attttgtagag gttttacttg cttaaaaaa      2220 cctcccacac ctcccctga acctgaacct gaaacataag aattc                      2265
```

<210> SEQ ID NO 5
<211> LENGTH: 37
<212> TYPE: DNA
<213> ORGANISM: Simian virus 40

<400> SEQUENCE: 5

```
ggggtaccag atggataaag ttttaaacag agaggaa                                37
```

```
<210> SEQ ID NO 6
<211> LENGTH: 37
<212> TYPE: DNA
<213> ORGANISM: Simian virus 40

<400> SEQUENCE: 6
gggaattctt atgtttcagg ttcaggttca gggggag                              37

<210> SEQ ID NO 7
<211> LENGTH: 30
<212> TYPE: DNA
<213> ORGANISM: Simian virus 40

<400> SEQUENCE: 7
ggggctagca ataaaatatc tttattttca                                      30

<210> SEQ ID NO 8
<211> LENGTH: 30
<212> TYPE: DNA
<213> ORGANISM: Simian virus 40

<400> SEQUENCE: 8
ggggctagcg agaaatgttc tggcacctgc                                      30

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: Synthetic
      forward primer for amplification of vector

<400> SEQUENCE: 9
cgactgtgcc ttctagttgc cagcc                                           25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence: Synthetic
      reverse primer for amplification of vector

<400> SEQUENCE: 10
ccagcatgcc tgctattgtc ttccc                                           25

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      forward primer for amplification of enhancer

<400> SEQUENCE: 11
ttgcatgaag aatctgctta ggg                                             23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      reverse primer for amplification of enhancer

<400> SEQUENCE: 12
atataggcct cccaccgtac acgc                                            24
```

```
<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      reverse primer for amplification of enhancer

<400> SEQUENCE: 13
ccaaagtcag gttgatgagc at                                              22
```